United States Patent [19]

Kaufman

[11] 4,430,013
[45] Feb. 7, 1984

[54] DISPOSABLE SWAB ARTICLE

[76] Inventor: Jack W. Kaufman, 357 Frankel Blvd., Merrick, N.Y. 11566

[21] Appl. No.: 322,857

[22] Filed: Nov. 19, 1981

Related U.S. Application Data

[63] Continuation of Ser. No. 59,659, Jul. 23, 1979, abandoned.

[51] Int. Cl.³ ............................................. A47L 13/17
[52] U.S. Cl. .................... 401/132; 401/196; 401/133; 604/3
[58] Field of Search ............. 401/132, 196, 133; 128/269, 267, 268; 222/94, 92, 107; 15/244 R; 604/3

[56] References Cited

U.S. PATENT DOCUMENTS

| | | | |
|---|---|---|---|
| 2,517,027 | 8/1950 | Rado | 222/94 |
| 3,239,105 | 3/1966 | Woodson | 222/94 |
| 3,315,801 | 4/1967 | Lowry | 222/94 X |
| 3,369,267 | 2/1968 | Friedland et al. | 401/132 |
| 3,636,922 | 1/1972 | Ketner | 401/132 X |
| 3,704,072 | 11/1972 | Kaufman | 401/132 X |
| 3,826,259 | 7/1974 | Bailey | 401/132 |
| 3,847,151 | 11/1974 | D'Alessandro | 401/133 X |
| 3,986,640 | 10/1976 | Redmond | 222/541 X |
| 3,998,559 | 12/1976 | Hoyt | 401/132 |
| 4,084,910 | 4/1978 | La Rosa | 401/133 |
| 4,140,409 | 2/1979 | Deuries | 401/132 |
| 4,173,978 | 11/1979 | Brown | 128/269 |
| 4,218,155 | 8/1980 | Weidner | 128/269 X |
| 4,236,652 | 2/1980 | Beguhn | 222/92 |

FOREIGN PATENT DOCUMENTS

| | | | |
|---|---|---|---|
| 2058139 | 5/1972 | Fed. Rep. of Germany | 401/132 |
| 2430404 | 1/1976 | Fed. Rep. of Germany | 401/132 |
| 2705347 | 8/1978 | Fed. Rep. of Germany | 401/132 |
| 2751078 | 5/1979 | Fed. Rep. of Germany | 222/107 |
| 485981 | 2/1918 | France | 128/269 |
| 1263715 | 5/1961 | France | 401/132 |
| 1434159 | 2/1966 | France | 15/244 R |
| 16547 | of 1915 | United Kingdom | 128/269 |

Primary Examiner—Steven A. Bratlie
Attorney, Agent, or Firm—Lackenbach, Siegel, Marzullo, Presta & Aronson

[57] ABSTRACT

This invention relates to disposable swab articles and other like packages comprising an applicator package having distal ends and having a foam applicator pad and a backing member adjacent thereto. The backing member has at least one reservoir and being formed of a relatively rigid, flat sheet material and a formed material for containing the contents of the reservoir therebetween. The flat sheet material has a slit or weakened portion in the surface of the material and the slit or weakened portion is transversely disposed of the flat sheet material, so that the slit or weakened portion is ruptured upon forcing the distal ends toward each other about the slit or weakened portion. The contents of the reservoir are thereby released into the foam applicator pad upon pressure deforming the formed material containing the reservoir.

8 Claims, 23 Drawing Figures

DISPOSABLE SWAB ARTICLE

This is a continuation of application Ser. No. 059,659, filed July 23, 1979 (now abandoned).

BACKGROUND AND SUMMARY OF THE INVENTION

Known in the prior art is a package for a flowable product, namely U.S. Pat. No. 3,986,640, granted Oct. 19, 1976 to Sanford Redmond. This patent teaches a package for a flowable product wherein the package includes a relatively stiff, but flexible material and a flexible material between which the flowable product to be packaged is contained and around which flowable product the materials are affixed to each other. The relatively stiff, but flexible material is cut through or partially through in a pattern so as to form at least one tongue and one opening and, when cut through, at least one side of the relatively stiff, but flexible material, at least in the area of the cut pattern, being covered with a sealant, which sealant preferably is a foil, the package, when bent, opening up along the cut pattern to dispense the flowable product from the package. The patent also discloses and teaches the flexible material which is used for making such a package.

One of the disadvantages of this package is the uncontrollable rate at which the flowable material is squeezed and discharged out of the package. Due to its form of construction, there is no control to the flow from the package, and that it does not teach any specific type of packages, such as applicator packages for specific needs in the medical profession. Also, the package of U.S. Pat. No. 3,986,640 does not teach the utilization of a multi-cavity reservoir for storage of the flowable product. With such a multi-cavity applicator package, one can achieve a controllable flow of the product from the package during use. Accordingly, although the prior art package noted herein functions in dispensing a flowable product from the package, it lacks the teaching of specific applicator packages which can be used in diverse applications. Thus, the packages of the present invention overcome the problems heretofore encountered with this prior art package and overcomes the disadvantages, and provides a number of applicator packages which have specific applications, particularly in the medical and veterinarian fields. Other packages for use in still other fields are also disclosed in the instant application.

Accordingly, one of the primary objects of the present invention is to provide an improved package, such as a swab package, embodying a foam applicator pad and a pair of members comprising a backing member of a relatively rigid, flat sheet material adjacent the applicator pad, and a formed material for containing the flowable product in a reservoir formed in said material and captured between said two members. The flat sheet material is provided with a slit or weakened portion in the surface of said material, and the slit or weakened portion is transversely disposed so that upon rupturing it by forcing the opposite ends of the applicator package toward each other about the slit or weakened portion, thereby enabling the contents of the reservoir to be released into the foam pad upon pressure deforming the formed material.

The foregoing object and other objects of the present invention will become apparent upon reading the following specification and referring to the accompanying drawings, which form a material part of this disclosure.

The invention accordingly consists in the features of construction, combination of elements, and arrangements of parts, which will be exemplified in the preferred constructions hereinafter described, and of which the scope will be indicated by the claims.

BACKGROUND OF THE INVENTION

This invention generally relates to swab articles, such as swab packages, swab sticks or applicators, scrub brushes with a swabbing or wiping surface, and to other similar type packages adapted for use as bandaids, inhalants and the like, such as skin preping or pre-operative scrubs having clensing agents, surgical scrubs, skin preps for cardiac electrodes and tincture or dye applicators, skin patch testing and through-the-skin dispensing of hormones or medicaments including time release formulations (such as insulin time release compounds). The swab packages of the invention are basically of the rupturable type embodying a receptacle for fluids, such as ointments, powders, germicides, liquids, gels, pastes, etc. Also, the swab packages include an applicator pad or surface or other like structure, and may be, if desired, suitably packaged with an overwrap to provide sterility.

As best shown in FIGS. 1–4, there is shown a swab package 10 embodying a receptacle or reservoir 12 and an externally mounted applicator 14, such as a gauze pad, plastic foam pad or synthetic cotton or fabric pad. The plastic foam material may comprise a urethane foam material or a natural latex foam. The construction of the receptacle or reservoir 12 is basically of the type disclosed in U.S. Pat. No. 3,986,640 as noted hereinbefore, and all of the teachings of said patent are hereby incorporated herein and form a part of this application. Thus, for example, with the present invention, the receptacle 12 may comprise on one side thereof a thin, relatively stiff laminate type of plastic sheet material 16, such as an extruded polystyrene, acrilonitride or copolymer with polystyrene with or without special coatings, such as vapor or gas barriers or heat sealants or bonding coats. The material may be, if desired, initially treated by stretching so as to orient the structure for providing additional strength in one direction only, whereby the material is capable of splitting easily in a direction orthogonal thereto, provided a score line or other weakened area 18 is made a part of the receptacle 12. Such a score or cut line or weakened area 18 is provided on the side or surface to which the applicator 14 is mounted or otherwise secured to the receptacle 12, by means such as adhesives, heat sealing, ultrasonic or electronic impulse bonding or other like securing means. Subsequent to the stretching of the base material, the material is then further provided with any desired laminate coating, such as spraying, or adhering another sheet of material directly on the base material.

The periphery 20 of the receptacle 12 is provided with a marginal seal such as a heat seal, to retain the fluid in said receptacle 12 from escaping therefrom until the receptacle 12 is fractured or ruptured, as will be further described herein in greater detail.

Figures 1, 2:
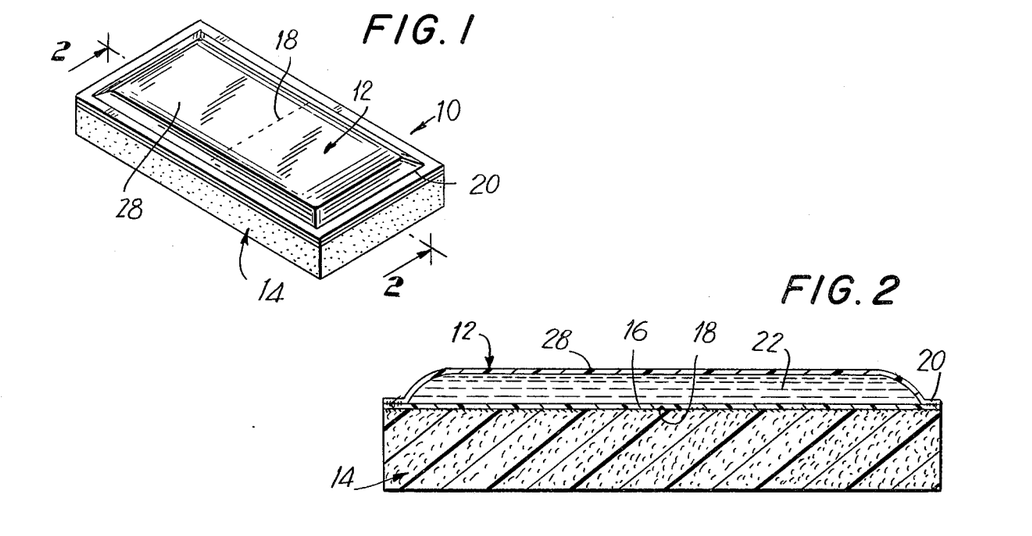
FIG. 1 is a top perspective view of a swab package of the present invention with an externally disposed wiper.
FIG. 2 is a cross-sectional view taken along the line 2—2 of FIG. 1.
Figures 3, 4:
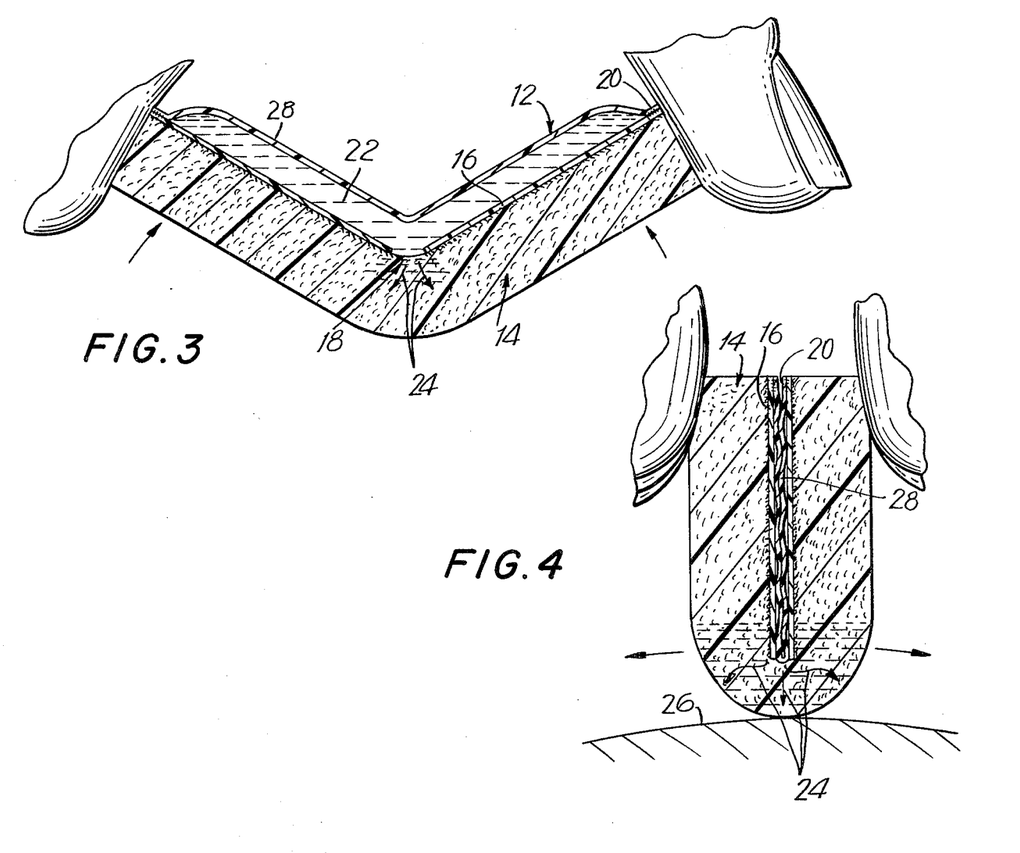
FIG. 3 is a view similar to that of FIG. 2, but with the swab package partially folded back upon itself to commence breaking of the rupturable seal.
FIG. 4 is a view similar to that of FIG. 3, but showing the swab package in use where the rupturable seal is completely broken and the contents of the package penetrates the wiper and is applied to a surface, such as a body.

In FIGS. 3–4, the package of FIGS. 1 and 2 is shown initially partially opened by bending or folding opposite ends of the package 10, thereby weakening the preweakened area or zone 18 so as to finally rupture same. The fluid 22 is thus released to flow directly into the applicator 14, as shown by the arrowheads 24. In FIG. 4, the receptacle 12 is shown completely collapsed by being squeezed to release substantially all of the contents of the cavity containing said fluid 22 so as to be wiped or applied on a surface 26, such as a body.

The upper exposed surface 28 is preferably a thin-coated foil, a single plastic layer, such as polyethylene or a laminate sheet material which is capable of being squeezed and compressed so as to meter out the contents of the reservoir and to progressively expell the fluid contents of the receptacle 12 when the package 10 is squeezed between one's thumb and forefinger or against a surface, as best shown in FIGS. 4, 6, 9, 11 and 15. The inside surface of the foil or other sheet material is generally coated or laminated with a polyethylene or polyester which provides the sealing surface and a surface which is chemically compatable for many fluids, such as inhalants, gels, ointments, liquids such as povidone iodine, (Hibitane, Hibiclens-trademark of Stuart Trust Pharmaceutical Co. a division of I.C.I., USA of Wilmington, Del.), chlorohexadine solutions, alcohol solutions, dyes, detergents, shampoos, or other germicidal compositions. In this connection, the packages of the present invention are generally designed for medical or veterinarian use, since they are of the disposable type after a single use or application. Other applicators, such as in the cosmetic industry where a liquid, gel or creams are used may be packaged and are considered within the scope of the present invention. For example, liquid make-up or make-up removers, hair coloring 'or dye' are all capable of being used with the applications of the present invention.

Using an upper surface 28 made of a plastic or synthetic material, such as polyethylene which has some memory when squeezed, the release of finger pressure would tend to cause or generate a vacuum and some of the fluid deposited on a body surface 26 would be sucked back through the foam which might be desired when an excess of the medicament or dye has been applied on a body surface or other area.

Figures 5, 6, 7, 8, 9:
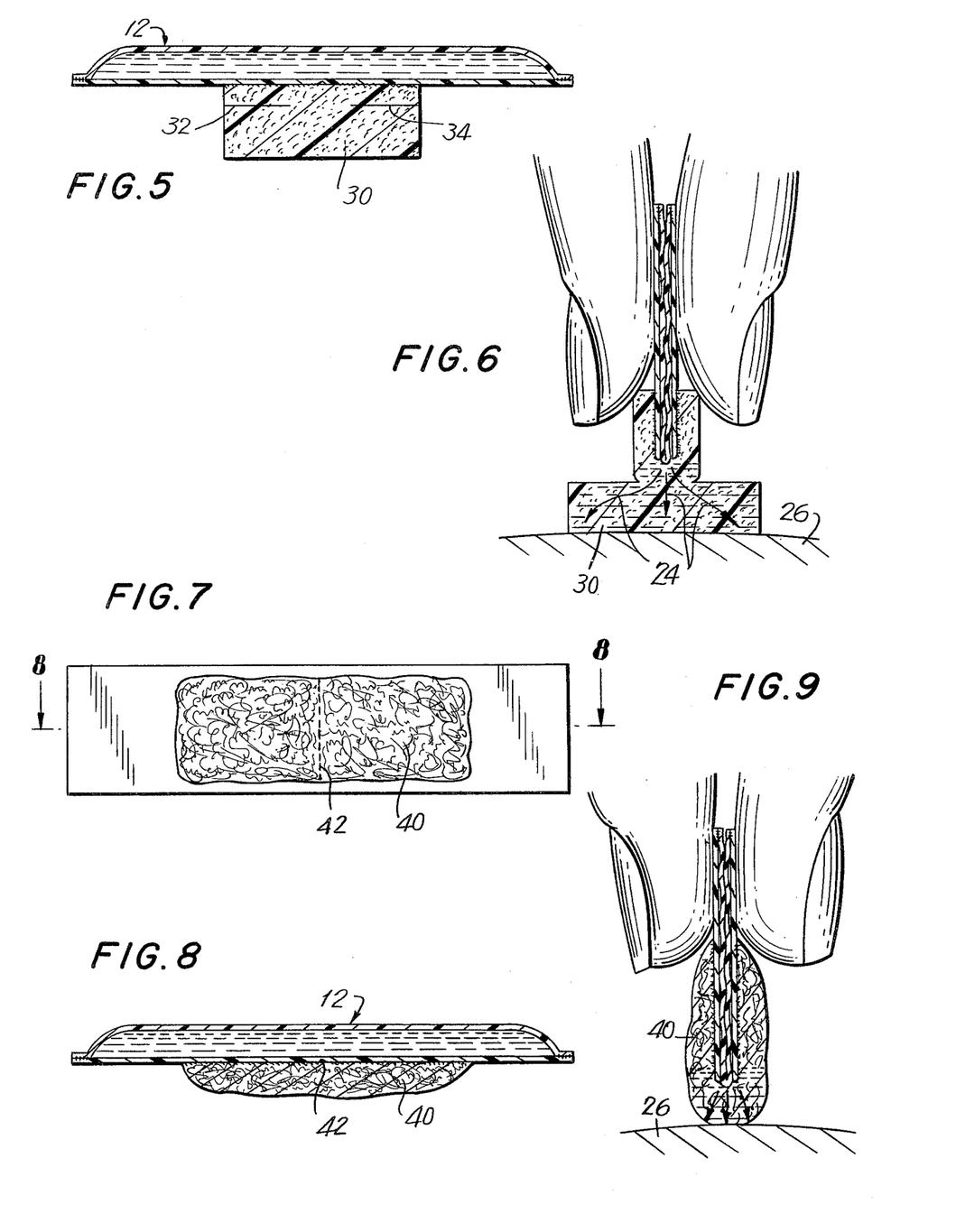
FIG. 5 is an alternate modification in cross-section of the swab package embodying a centrally disposed "split or butterfly type" sponge which in use provides a large wiping surface and improved means for gripping the swab package.
FIG. 6 is a cross-sectional view similar to that of FIG. 4, but showing the swab package of FIG. 5 in use.
FIG. 7 is a bottom plan view of another swab package with a centrally disposed sponge, similar to that of FIG. 1, but with a smaller wiping surface.
FIG. 8 is a cross-sectional view taken along the line 8—8 of FIG. 7.
FIG. 9 is a cross-sectional view similar to that of FIG. 6, but showing the swab package of FIG. 7 in use.

In FIGS. 5–9, there is shown alternate embodiments of the invention. FIGS. 5 and 6 illustrate a device or swab package similar to that of FIGS. 1–4, but with a small split applicator pad 30 which forms a "butterfly" or inverted T with the large limb or top of the T forming the wiping applicator surface. The pad 30 is centrally disposed on the device and has a pair of slits 32, 34 which provides a much larger wiping surface of the head portion as compared to the head portion or wraparound wiping surface of the device shown in FIGS. 1–4. One of the advantages of this type of construction is that it prevents a doctor's fingers from coming in contact with the body 26, should the fingers slip downwardly or forwardly. If they did, the fingers would simply contact the top or upper side of the wiping applicator surface. With this type of structure, a denser or stiffer urethane foam material having less pores per inch is preferred as the outwardly extending ends should stay in contact with the body or surface 26 and not flap loosely or curl when the applicator is vigorously wiped back and forth.

Figure 13:
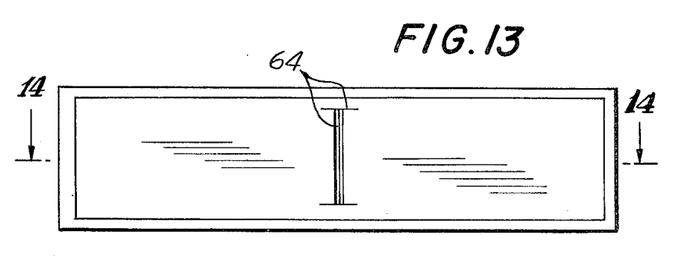
FIG. 13 is a view similar to that of FIG. 12, but showing a like swab package with a transverse rupture line or seal.

The modifications of FIGS. 7–9 illustrate another centrally disposed applicator pad 40 suitably affixed to the lower surface of the receptacle 12. In this case, the pad 40 is of a generally small size so as to preclude or reduce the chances of the fingers of a doctor from coming in contact with the foam or sponge-like applicator pad 40 and thereby contaminating same. The cut or score line 42 may be suitably formed as a single strike or line, double line or row. Also, the line or cut may be straight or curved half moon or semi-lunar shaped or preferably can form the shape of a Roman numerial I, as best shown in FIG. 13. Other examples of the cut, score or weakened area are more particularly described in the aforesaid U.S. Pat. No. 3,986,640.

Figure 10:
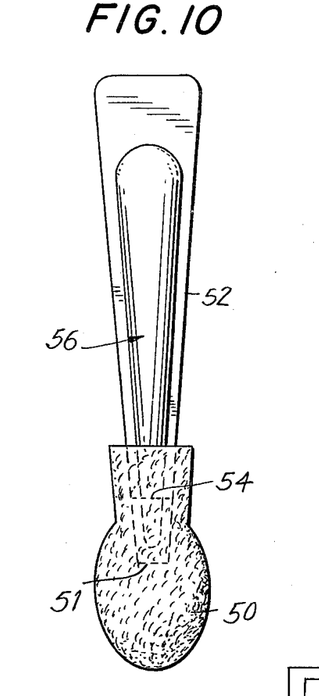
FIG. 10 is a plan view of another modification of the swab package with the sponge swab portion disposed at one end of the package and with the rupturable seal area also disposed at the same end of the package.
Figure 11:
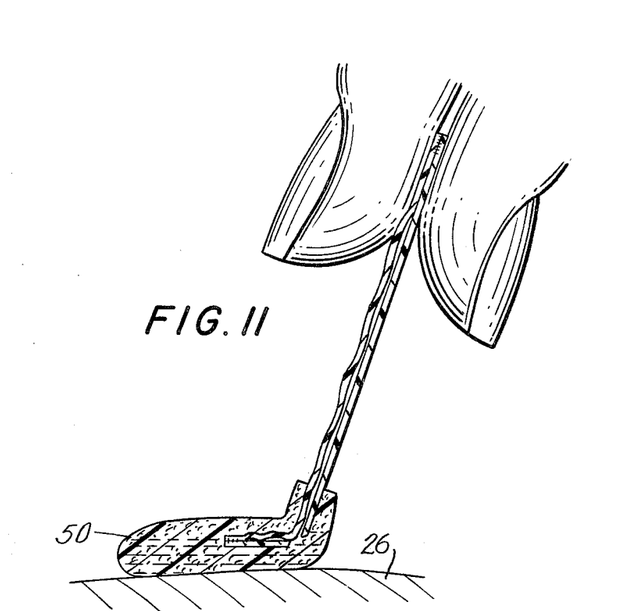
FIG. 11 is a cross-sectional view of the embodiment of FIG. 10, showing the swab package in use.

FIGS. 10 and 11 show a modified swab applicator embodying a foam applicator tip 50 suitably affixed to the end 51 of a stem or handle 52 proximal to the cut or scored line 54 of the receptacle 56. In such structure, it is preferable to use a stiffer material in lieu of the foil material. However, it is important to note that the stiffer material should be properly oriented so that the score or cut line can be easily ruptured (oriented transverse to the stretched direction of the material). Although the fluid contents of the receptacle 56 will be expelled at the proximal end of the foam pad 50, it will swish easily to the distal end of the pad as the fluid is further forced out of the receptacle 56. It should also be noted that the end of the stem or handle 52 may be affixed to an outside surface of the receptacle 56, in lieu of being internally disposed in the foam pad 50 as shown in FIGS. 10 and 11.

In FIGS. 12-15, the applicator pad 60 is internally disposed within the cavity of the receptacle or reservoir. One of the advantages of this structure is that since the package forms in effect a totally sealed construction, there is no chance of contamination of the applicator pad until rupture and actual use. With the other types of swab packages, an outer wrap is necessary to maintain the applicator pad from particulate matter and also to retain sterility of the overall package prior to its use. However, as a practical matter, a plurality of non-overwrapped applicators may be conveniently dispensed from a multiple dispenser box which initially may be suitably sealed and sterilized when initially packed at the factory. Of course, after the package is opened, sterility cannot be guaranteed for the rest of its contents.

Although not shown because the foam is compressed, it is extremely preferable for the sponge or foam area in the vicinity of the cut or score line to have a transverse protrusion, head or thickened portion facing said cut or score line. This thickened portion or protrusion 62 is shown protruding from the cut or score line 64. The top or upper surface 66 of the receptacle 68 is preferably provided with a depression forming a rib 70. This rib 70 serves to assist in pushing or forcing said applicator pad 60 through said cut or score line 64, when the package is bent or folded during use.

Figure 12:
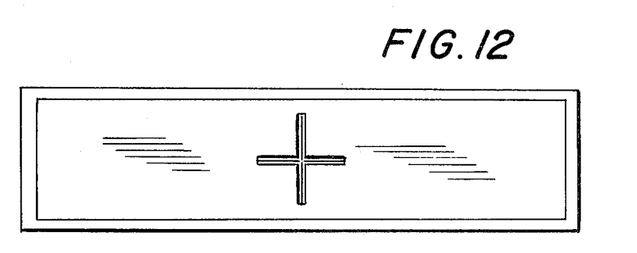
FIG. 12 is a bottom plan view of a further modification of the swab package wherein the sponge is internally disposed within the swab package and has a large cross-cut rupturable seal.
Figure 14:
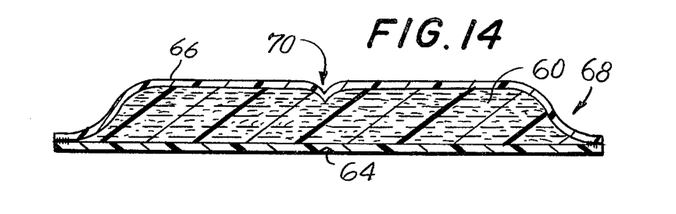
FIG. 14 is a cross-sectional view taken along the line 14—14 of FIG. 13.
Figure 15:
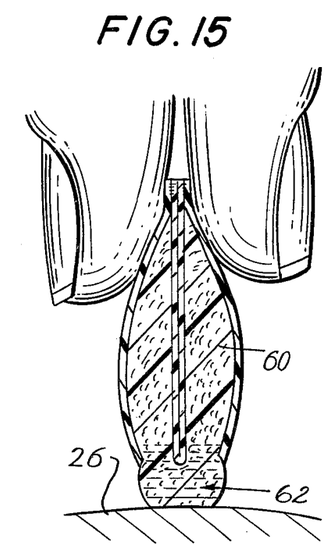
FIG. 15 is a cross-sectional view similar to that of FIGS. 4, 6, 9 and 11, but illustrating the internally disposed sponge wiper of FIGS. 12-14 protruding from the ruptured seal when in use.

FIG. 12 merely illustrates a cross type of cut or score line, in lieu of a straight line or line having the shape of Roman numeral I, as shown in FIGS. 13-15. Even with this type of slitting, the pad 60 protrudes from the package, but only in a limited circular area or zone which may be desirable for certain applications, in contrast to the larger transverse wiping surface formed when the alternate package constructions are bent or folded.

Figure 16:
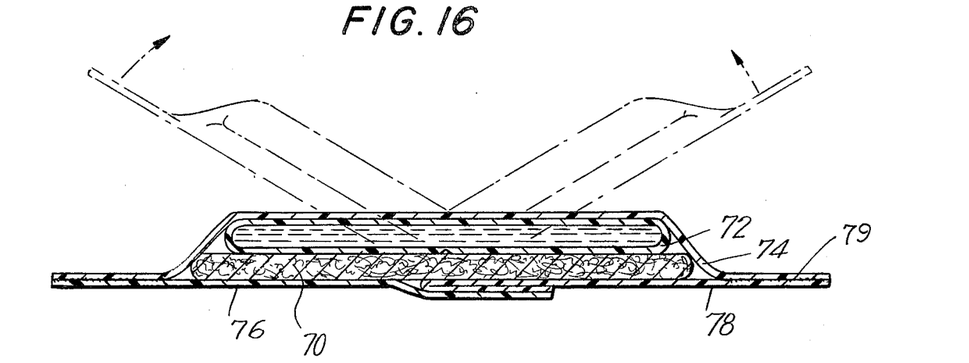
FIG. 16 is a cross-sectional view of a "bandaid" modification of the swab package of the present invention.

A surgical dressing or "Band-Aid" type of applicator package is shown in FIG. 16. As shown therein, the dressing is generally in the form of a cotton or synthetic pad 70 affixed to the receptacle or reservoir 72 and both elements are suitably secured to an outer adhesive type material 74 having one or more removable layers or coverings, such as siliconized papers. Preferably, a pair of such pealable papers 76 and 78 is provided to protect the adhesive 79 and its tape qualities and to maintain the integrity of the overall package, particularly the cotton or synthetic pad 70. In use, the protective paper material may be removed first and then the receptacle can be cracked or ruptured to dispense the fluid into the dressing or pad 70 or the reverse procedure is also possible. The application of the dressing on a wound is akin to that of a "Band-Aid" or other like dressing with the addition of a self-contained medicament. This embodiment of the invention is also adapted for use as a skin patch tester or through-the-skin dispenser or infuser.

Figure 17:
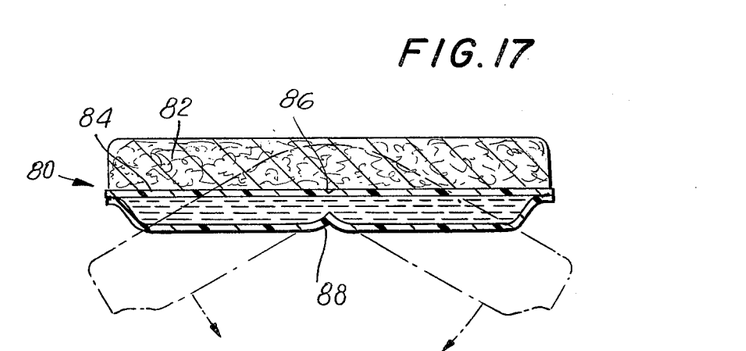
FIG. 17 is a cross-sectional view of yet a further modification of the invention with dual chambers and rupturable seals adapted for use as an inhaler, such as an ammonia inhaler.

Another modified package is the inhalant 80 shown in FIG. 17. As shown therein, the cotton or cellulose, rayon or urethane pad 82 is affixed to the receptacle 84 and when the receptacle 84 is bent or folded upon itself, the cut or score line 86 is ruptured causing the fluid to escape into the pad 82. The indentation or depression 88 in the package is like the depression 70 of the package shown in FIG. 14. Such a feature provides a wedge for pressing against the cut or score line 86 so as to easily cause the rupture of same without undue bending forces. In this construction, the pad 82 need not have a protective covering as it is merely used as a porous absorber for the inhalant material which is released from the receptacle 84 into the pad 82 upon squeezing the package together about the score line 86, as best shown by the phantom lines of FIG. 17.

Figures 18, 19:
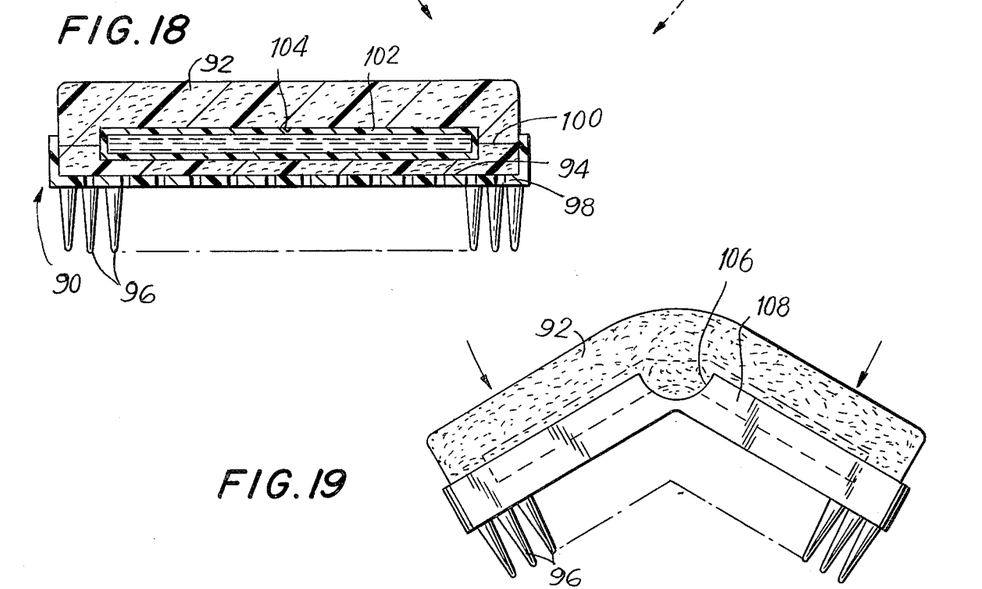
FIG. 18 is a cross-sectional view of another emboidment of the invention showing a scrub brush with bristles and with a rupturable package disposed within a sponge secured to the back of the brush.
FIG. 19 is a side elevational view of the scrub brush of FIG. 18, showing it slightly bent along a transverse plane so as to rupture the sealed package and release its contents into the sponge.

FIG. 18 shows a scrub brush 90 with bristles and with a rupturable package disposed within a sponge 92 secured to the base or well 94 on the back of the brush. The bristles 96 form part of the generally rigid and generally perforated backing element 98. This backing member 98 may have suitable sides to aid in retaining the sponge 92 which may be suitably secured, such as by adhesives, to the backing member 98. The sponge 92 may be suitably slit along a line 100 so as to accommodate a receptacle 102 containing a germicidal composition or other scrubbing or cleansing solution. The receptacle 102 is suitably weakened or scored at 104 so as to split in the central portion of the scrub brush or receptacle and release the composition or other cleansing solution into the sponge 92 when the brush is bent or folded about a weakened area or zone 106 on opposite longitudinal side walls 108 of the backing member 98, as best shown in FIG. 19. My co-pending patent application, Ser. No. 828,763, filed Aug. 29, 1977, now U.S. Pat. No. 4,181,446; granted Jan. 1, 1980 disclosed such a foldable brush which could be adapted to contain the receptacle 102. However, in such an arrangement, the width of the receptacle would be wider as the slit would have to be oriented longitudinally instead of transversely. Note that the germicidal solution may comprise povidine iodine, chlorohexedine, hexochlorphene, alcohol, etc. and/or a detergent in the form of powder or crystals which when suitably melted provide a cleansing, scrubbing and disinfecting composition. Other solutions, such as merthiolate, zephrin chloride in a liquid or a gel may also be used.

The relatively stiff or rigid sheet material having the weakened or scored zone is of a plastic, such as polystyrene or a copolymer thereof. In addition, a gas and/or a vapor barrier should be applied to the outer side of the receptacle to preclude water, vapor loss and entry of oxygen or evaporation of the receptacle's contents, such as alcohol. Such barriers may be coating or layers of materials, such as BARTUFF (a trademark of American Can Co.), SARAN (a Dow Chemical Co. trademark), Aclar, a fluorohalocarbon film, (a trademark of Allied Chemical Corporation), thin foil, etc. The score or cut pattern or patterns extend only partially through the material, and the use of a sealant or foil covering one or both outer faces of the sheet material may be used, if desired, where packaging requirements dictate such additional layers or coatings which serve other well known functions. For example, gas barriers, such as foil (aluminum) preclude loss of product or active ingredients of the stored product. Also, they tend to keep water or the alcohol context of the product stable in order to have a normal or extended sheld life for the product. Other backing types of laminates embodying aluminum foil which may be employed with the invention comprise foil and polyethylene; foil, polyester and polyethylene; or foil and a polyester.

Polyester and styrene sheets, however, do not exhibit as good gas and water barrier characteristics. Better gas and water barrier type packages are formed by butylated low density and high density polyethylene laminated to nylon, polyvinylidene chloride (Saran), acrylic, polyester, and Aclar and other suitable coatings.

It should also be noted that the type of material used depends on the product to be packaged. For example, iodine attacks foil chemically changing it to aluminum iodide, which is a white powder and the active iodine (free iodine) is thus lost because it has an affinity for the foil, thereby weakening the iodine solution (loss of the active or free iodine). A polyester coating, however, can be used to separate the iodine from the foil barrier. Bonding the layer together, heat sealing the seams and containing the product over long periods of time involve a constant search for better and stronger combinations of materials and coatings, so that a sound package is formed completely free of failure (leakage) or deterioration of shelf life where, say the active materials in the iodine solutions are dissipated gradually due to being absorbed or reacted with the polyester or polyethylene coatings.

In FIGS. 20-23, a further modifications of the invention are illustrated. As shown therein, a pair of reservoirs 100 and 102 having necked down portions 104 leading to a fanned out proximal portion 106. The function of the funneling or necked down effect is to provide a controllable flow or to slow down the flow rate of the fluid being forced out of the reservoirs 100 and 102. The fanned out portions 106 distribute the fluid more evenly over the entire transverse length of the swab material 108. In this embodiment, the swab material 108 is a urethane foam material folded about itself and shaped so as to form a half round adhered to each side of the weakened area 110. Although two reservoirs are shown, it is possible to provide a single reservoir with a pair of oppositely opposed sections joined together at a centrally disposed necked down portion having a further centrally disposed fanned out portion with the weakened area central to the fanned out area.

With a single reservoir, the fluid has a tendency to rush out into the foam or sponge and through it at an almost uncontrollable rate, thereby not uniformly wetting the entire sponge initially. Also, it passes through the sponge creating drips and spillage and generally messes up a neat and clean application of the fluid. Also, such a construction does not leave any further fluid in reserve for further use in scrubbing.

With a dual cavity unit, since the cavities are smaller and contain less fluid than a single cavity with the same total volume, there is more surface tension and less chance for fluid to spill out of the cavities during movement of the cavities in the web material which is being pulled through, filled and sealed on the same machine.

Figure 23:
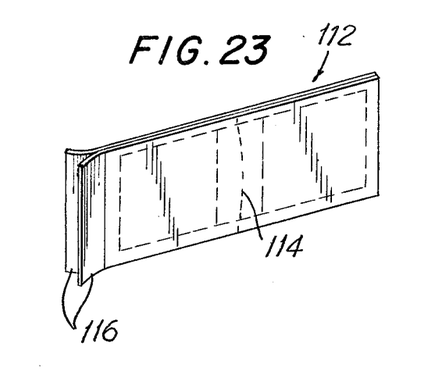
FIG. 23 is a perspective view showing the applicator package in a paper wrapper having a scored or weakened perforated zone permitting the foam to burst through the wrapper upon activation and use of the applicator.

In addition, this structure makes the reservoir portion more rigid because there is more definition implied by the configuration of a dual, or double necked down-fanned out reservoir. The multiple compound shapes or ribbing effect pressed into or vacuum formed in the foil laminate gives it superior strength which is not naturally inherent or formed in such materials. Thus, the swab is stronger and will crack more easily when desired and the limbs of the swab will meet in a better back-to-back fashion and have less likelyhood of sizzoring since the structure lends itself to a more sharper and distinct action when the package is activated by bending together the opposite ends for opening the reservoir. FIG. 23 shows an applicator package in a peripherally-sealed paper wrapper 112 having a scored or weakened transverse perforated line 114 which permits the foam pad or applicator to burst through the wrapper upon activation and use of the applicator package. This eliminates contamination of the foam pad in use. Of course, if desired, pealable end flaps 116 may be employed to conventionally open an end of the paper wrapper so as to provide access to the applicator.

Figure 20:
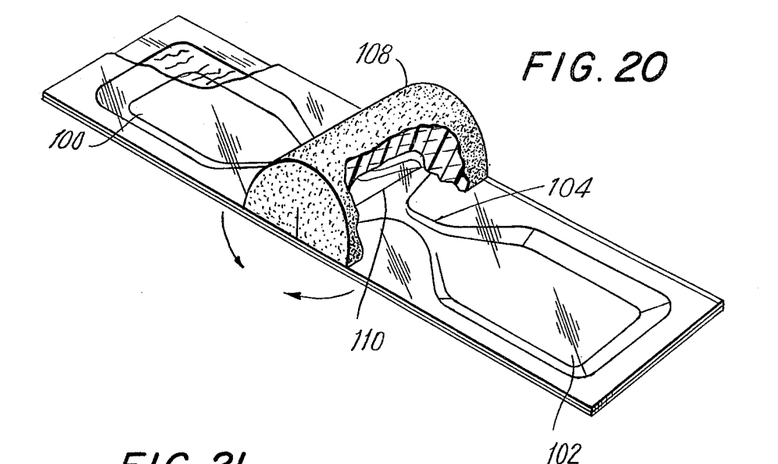
FIG. 20 is a perspective view of a further modification of the applicator package.
Figure 21:
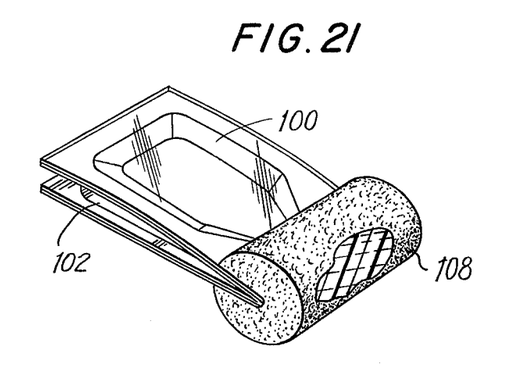
FIG. 21 is a perspective view of the embodiment of FIG. 20, but showing the applicator package in use with the distal ends thereof squeezed toward each other.
Figure 22:
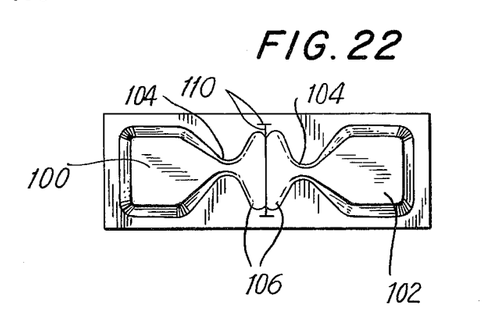
FIG. 22 is a rear plan view illustrating the back side of the applicator package of FIGS. 20–21.

It should also be recognized that the package of FIGS. 20-22 can be used to dispense an epoxy cement. One of the two reservoirs can store any conventional filler or epoxy resin and the other reservoir can store the appropriate hardener or activator. Such a two-component epoxy system can be designed with the necked portion 104 of each reservoir meeting adjacent each other at their ends in the center of the package below the split 110 which need not necessarily be transversely disposed across the entire width of the package. Of course, with such a construction, there would be no need for the fanned-out portions 106 as the metering of the epoxy would be just to a small spot or area where the split 110 would be provided in the immediate vicinity of the ends of the necked-down portions 104.

If a three or four cavity applicator system is desired for use in dying applications or other uses, the package can simply be arranged to contain, for example, two reservoirs on one or both sides by simply dividing the reservoir (100 or 102 or both) in half with a separation or barrier wall disposed horizontally or longitudinally down the center of the package. This construction could then be used in any system where three or four reservoir cavities are required.

Although the present invention has been described in some detail by way of illustration and example for purposes of clarity of understanding, it will, of course, be understood that various changes and modifications may be made in the form, details, and arrangements of the parts without departing from the scope of the invention as set forth in the following claims.

I claim:

1. An applicator package having distal ends comprising a foam applicator pad and having a backing member adjacent thereto: said backing member being formed of a relatively rigid, flat and stiff plastic sheet material having a vapor and gas barrier coating and a laminated deformable plastic coated foil material having at least one reservoir containing a flowable product, such as a liquid being sealed to said flat and stiff sheet material for containing the contents of said reservoir therebetween; said flat and stiff sheet material having a centrally disposed linear weakened portion in the surface of said flat and stiff sheet material and said weakened portion being transversely disposed of said flat and stiff sheet material with said foam applicator pad secured to the outer surface of said flat and stiff sheet material and centrally disposed over said weakened portion; said weakened portion rupturing upon forcing said distal ends of said applicator package towards each other and about said weakened portion, so as to compress the reservoir of said deformable plastic coated foil material by crushing opposite sides of said reservoir against each other such that substantially all of said flowable product in the reservoir can be controllably released into said applicator pad for wiping applications upon pressure completely deforming and collapsing said plastic coated foil material; and said foam applicator pad is a foam block having opposite slits partially through said foam block so that when said distal ends are squeezed together, the foam block assumes an inverted T-shape with a large wiping contact surface area.

2. The applicator package according to claim 1, wherein said weakened portion is centrally disposed in said flat sheet material.

3. The applicator package according to claim 2, wherein said foam pad extends along the central portion of said rigid, flat sheet material and is disposed so as to extend equally in opposite directions from said weakened portion.

4. The applicator package according to claim 3, wherein said reservoir is a cavity in the plastic coated foil material and forms a central pinched funnel structure and oppositely disposed reservoir portions with a narrow necked channel therebetween and opposite the zone where said transverse weakened portion is located.

5. The applicator package according to claim 4, including a fanned out portion provided centrally of said narrow necked channel with said weakened portion located centrally and parallel to said fanned out portion.

6. The applicator package according to claim 4, including an outer wrapper for protecting said applicator.

7. The applicator package according to claim 6, wherein said wrapper is peripherally sealed except for a pealable end providing access to said applicator.

8. The applicator package according to claim 6, wherein said wrapper is peripherally sealed and one side thereof has a centrally disposed transverse perforated line opposite to said foam pad, so that said applicator is activated within said wrapper and said wrapper is caused to rupture at said perforated line, whereby said foam pad protrudes therefrom.

* * * * *